US012508390B2

(12) United States Patent
Orr et al.

(10) Patent No.: US 12,508,390 B2
(45) Date of Patent: Dec. 30, 2025

(54) RESPIRATORY FLUID FLOW CONTROL DEVICE AND METHOD OF USING SAME

(71) Applicant: Dynasthetics, LLC, Salt Lake City, UT (US)

(72) Inventors: Joseph Orr, Park City, UT (US); Eric Youngberg, Layton, UT (US); Kyle M. Burk, Farmington, UT (US); Trey Blackwell, Lehi, UT (US)

(73) Assignee: Dynasthetics, LLC, Salt Lake City, UT (US)

( * ) Notice: Subject to any disclaimer, the term of this patent is extended or adjusted under 35 U.S.C. 154(b) by 910 days.

(21) Appl. No.: 17/737,829

(22) Filed: May 5, 2022

(65) Prior Publication Data

US 2023/0355912 A1 Nov. 9, 2023

(51) Int. Cl.

| | |
|---|---|
| ***A61M 16/12*** | (2006.01) |
| ***A61M 16/00*** | (2006.01) |
| ***A61M 16/06*** | (2006.01) |
| ***A61M 16/08*** | (2006.01) |
| ***A61M 16/10*** | (2006.01) |

(52) U.S. Cl.

CPC ...... *A61M 16/127* (2014.02); *A61M 16/0816* (2013.01); *A61M 16/1005* (2014.02); *A61M 16/107* (2014.02); *A61M 2016/0027* (2013.01); *A61M 16/06* (2013.01); *A61M 16/085* (2014.02); *A61M 16/0858* (2014.02); *A61M 2202/0208* (2013.01); *A61M 2205/3334* (2013.01); *A61M 2205/42* (2013.01); *A61M 2205/7518* (2013.01); *A61M 2206/20* (2013.01)

(58) Field of Classification Search

CPC .............. A61M 16/06; A61M 16/0816; A61M 16/0833; A61M 16/085; A61M 16/0858; A61M 16/1005; A61M 16/107; A61M 16/125; A61M 16/127; A61M 2016/0027; A61M 2202/0208; A61M 2205/3334; A61M 2205/42; A61M 2205/7518

See application file for complete search history.

(56) References Cited

U.S. PATENT DOCUMENTS

| | | | | |
|---|---|---|---|---|
| 3,850,171 A * | 11/1974 | Ball | A61M 16/06 | 128/204.25 |
| 3,913,607 A * | 10/1975 | Price | A61M 16/127 | 431/114 |
| 2013/0199535 A1* | 8/2013 | Dhuper | A61M 16/209 | 128/204.25 |
| 2014/0053841 A1* | 2/2014 | Ratner | A61M 16/0057 | 128/204.25 |
| 2023/0121027 A1* | 4/2023 | Johnson | A61M 16/201 | 128/204.25 |

FOREIGN PATENT DOCUMENTS

WO WO-2015128716 A1 * 9/2015 .......... A61M 16/127

* cited by examiner

*Primary Examiner* — Joseph D. Boecker

(74) *Attorney, Agent, or Firm* — Dentons Durham Jones Pinegar; Sarah W. Matthews

(57) ABSTRACT

An adaptor for generating flow includes an adaptor housing body. The distal end of the body has an oxygen inlet that extends extending into an interior of a distal air intake portion. The oxygen inlet has a nozzle with at least two apertures for directing oxygen into an interior of a distal air intake portion. The distal air intake portion includes at least one air inlet port to allow air to be drawn into the interior of the distal air intake portion, and a flow-resisting media covering at least a portion of the at least one air inlet port.

20 Claims, 10 Drawing Sheets

RESPIRATORY FLUID FLOW CONTROL DEVICE AND METHOD OF USING SAME

TECHNICAL FIELD

The present disclosure relates generally to respiratory assist devices. More specifically, the disclosure relates to a respiratory fluid control device or adaptor for delivering oxygen to a patient and method of using the same.

BACKGROUND

Positive airway pressure therapies are used for the treatment of various respiratory conditions including both central apnea and obstructive apnea. During sleep or sedation, it is common in patients for the muscles that normally hold the upper airway open to relax so that airway tissues partially occlude or obstruct the airway, preventing adequate gas flow to the lungs. In many patients that are in a relaxed state such as sleeping or who have received sedative drugs, the muscles of the upper airways are relaxed to such an extent that any effort to inhale by the patient collapses the airway and obstructs gas flow restricting ability to draw in breathable gas. The negative pressure created as the patient tries to draw gas into the lungs pulls the airway closed even more, exacerbating the problem.

Positive airway pressure (PAP) therapies use a tightly sealed breathing mask and a source of flowing breathable gas to create positive pressure in the airway. This positive pressure supports the airway opening such that it does not collapse as the patient inhales. The flow generator used for PAP must have sufficient flow to supply patient inhalation volume and compensate for any mask leak. The flow generator must also have sufficient positive pressure to counterbalance any negative pressures created by the patient during inhalation. Continuous positive airway pressure, or CPAP, is a specific PAP therapy that continuously applies a specific prescribed pressure to the airways throughout every cycle of the breath. CPAP forces the airway to stay open during inhalation so that breathable gas can pass freely into the lungs on demand even when the airway opening is relaxed.

SUMMARY OF DISCLOSURE

According to the present disclosure, an adaptor for generating flow comprises: an adaptor housing body, the adaptor housing body comprising a distal end and an open proximal end for attachment to a patient interface; the distal end of the adaptor housing body having an oxygen inlet, the oxygen inlet comprising a coupler on an exterior side for connection to an oxygen source to convey pressurized oxygen from a pressurized oxygen source in connection with the coupler to the adaptor; the oxygen inlet extending into an interior of a distal air intake portion, and the oxygen inlet having a nozzle with at least two apertures for directing oxygen into an interior of a distal air intake portion; and the distal air intake portion comprising at least one air inlet port to allow air to be drawn into the interior of the distal air intake portion, and a flow-resisting media covering at least a portion of the at least one air inlet port.

According to another aspect, an adaptor for generating flow comprises: an adaptor housing body, the adaptor housing body extending from a distal end to an open proximal end, the open proximal end for attachment to a patient mask; the distal end of the adaptor housing body having an oxygen inlet for coupling to an oxygen source, the oxygen inlet extending into an interior of a distal air intake portion, and the oxygen inlet having a nozzle with at least one aperture for directing oxygen into the interior of a distal air intake portion; and the distal air intake portion comprising at least one air inlet port to allow ambient air to be drawn into the interior of the distal air intake portion, a flow-resisting media covering at least a portion of the at least one air inlet port.

According to yet another aspect, an adaptor for generating flow comprises: an adaptor housing body, the adaptor housing body comprising a distal end and an open proximal end for attachment to a patient interface; the distal end of the adaptor housing body having an oxygen inlet, the oxygen inlet comprising a coupler on an exterior side for connection to an oxygen source, the oxygen inlet extending into an interior of a distal air intake portion, and the oxygen inlet having a nozzle with at least two apertures for directing oxygen into an interior of a distal air intake portion; the distal air intake portion comprising at least one air inlet port to allow air to be drawn into the interior of the distal air intake portion, a proximal portion in communication with the distal air intake portion, the proximal portion forming a throat having a first circumference and an outlet having a second circumference for connection to a patient interface, the first circumference being smaller than the second circumference, the proximal portion further comprising at least one of a pressure measuring port and a gas sampling port.

BRIEF DESCRIPTION OF DRAWINGS

The drawings are illustrative and not limiting of the scope of the invention which is defined by the appended claims. Not every element of the disclosure can be clearly displayed in a single drawing, and as such not every drawing shows each element of the disclosure. The components in the drawings are not necessarily to scale relative to each other. Like reference numerals designate corresponding parts throughout the several views.

DETAILED DESCRIPTION

The present disclosure relates generally to a system and device for improved oxygen delivery to a patient. The adaptor or respiratory fluid control device described herein delivers a higher oxygen concentration when the flow exiting the adaptor is reduced during the end expiratory pause of the patient's breath or other phases of the breath during which flow through the outlet port is restricted, as described in more detail below. This results in a high concentration of oxygen in the patient's mask prior to the beginning of the patient's inhalation.

As used herein, "proximal" refers to a portion of the system or device that is closer to the patient when in use, and "distal" refers to a portion of the system or device that is farther from the patient when in use. For example, the device described herein may be attached directly to a patient's mask, with the proximal end of the device being connected to the mask (closer to the patient) and the distal end facing away from the mask. The system or device may be referred to as an "adaptor," and as used herein, "adaptor" means any type of fluid flow control apparatus, such as a flow generator, a Venturi adaptor, or any other device that can be connected to a patient interface (such as a mask) to input a high pressure oxygen flow into the adaptor and output from the adaptor a low pressure of oxygen and/or a low pressure of oxygen blended with ambient air. Patient interface could be a mask, an endotracheal tube, a supraglottic airway device (a laryngeal mask airway is common), etc.

Figure 1:
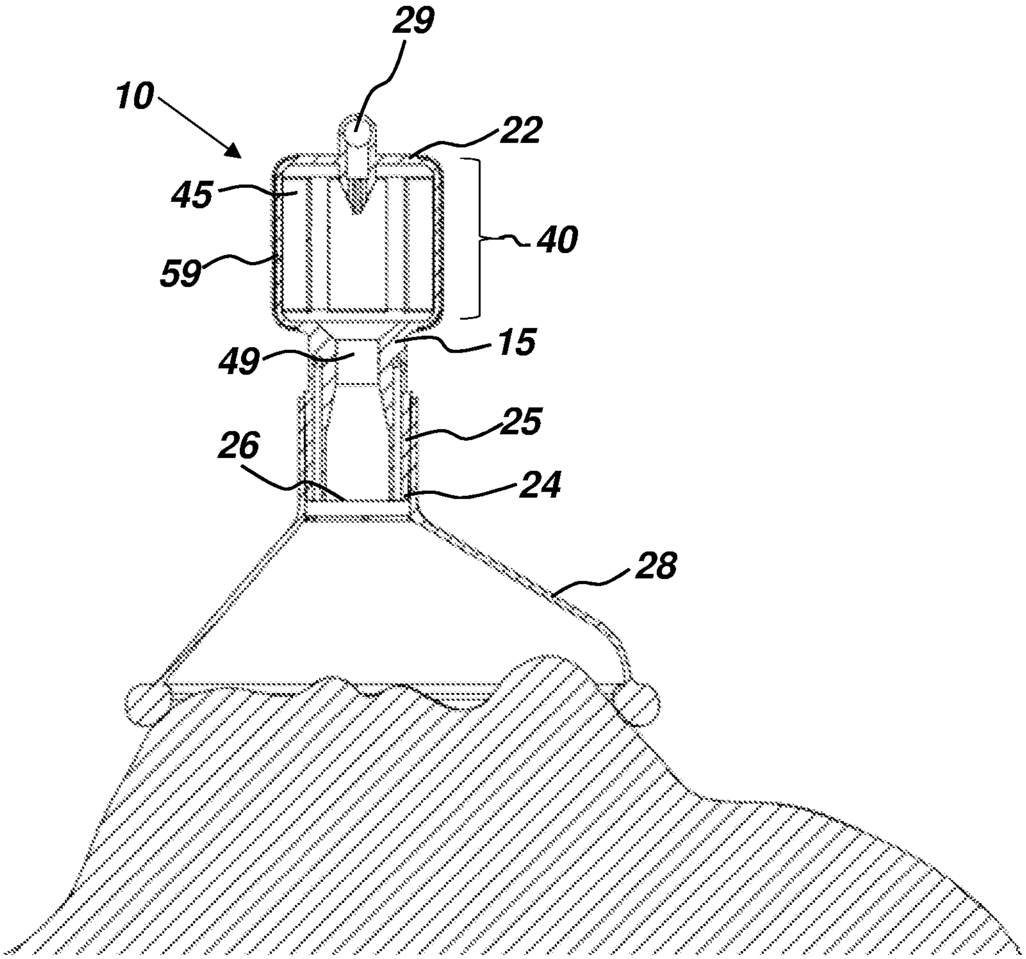
FIG. 1 is a side, elevation, cross-sectional view of an exemplary adaptor in place on a mask of a patient.

Referring to FIG. 1, an exemplary adaptor 10 generally includes an adaptor housing body 15 extending from a distal end 22 to a proximal end 24. The distal end 22 can have an oxygen inlet 29 (with a coupler 35 for attaching to an oxygen source) for inputting oxygen into the adaptor 10, and the proximal end 24 can have an outlet 26 or exit port for coupling to a patient interface, such as a mask 28.

The oxygen inlet 29 extends through the distal end 22 of the body 15, and directs oxygen through a nozzle to a distal air intake portion 40 in the interior of the body 15 as described in more detail below. Air inlet port(s) 45 allow air to also be drawn into the distal air intake portion 40, and a flow-resisting media 59 can cover at least a portion of the air inlet port(s) 45. The air drawn in from air inlet port(s) 45 mixes with oxygen directed to distal air intake portion 40 from the oxygen inlet 29. The mixed oxygen-air passes through a throat 49, to a proximal portion 25, and exits an outlet 26 to a patient interface (such as mask 28) coupled to the proximal portion 25.

Figure 2:
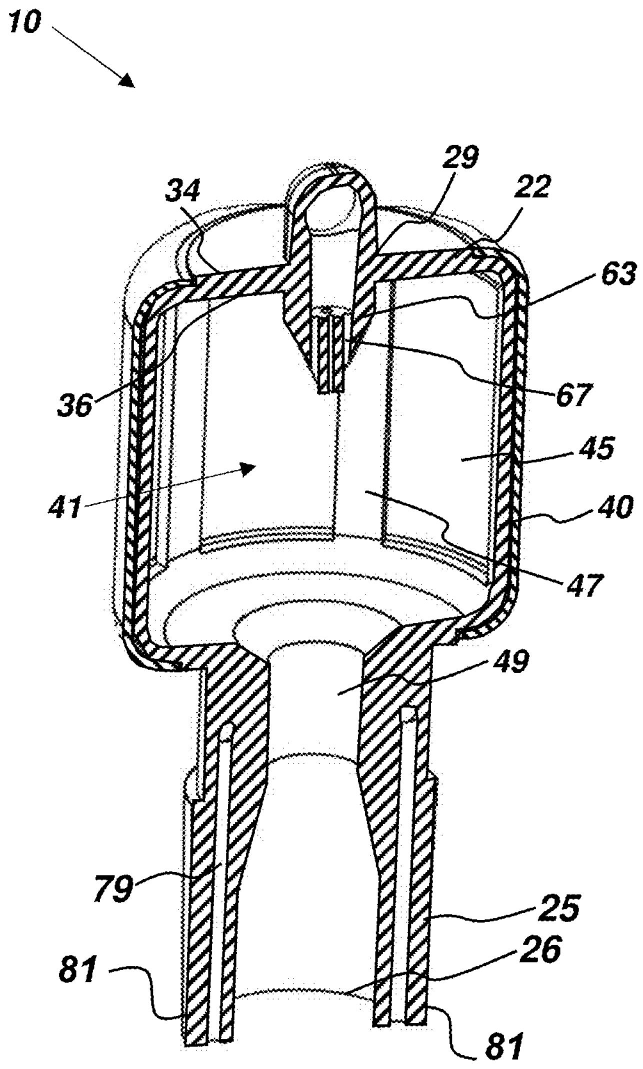
FIG. 2 is a perspective, cross-sectional view of an exemplary adaptor.
Figure 3:
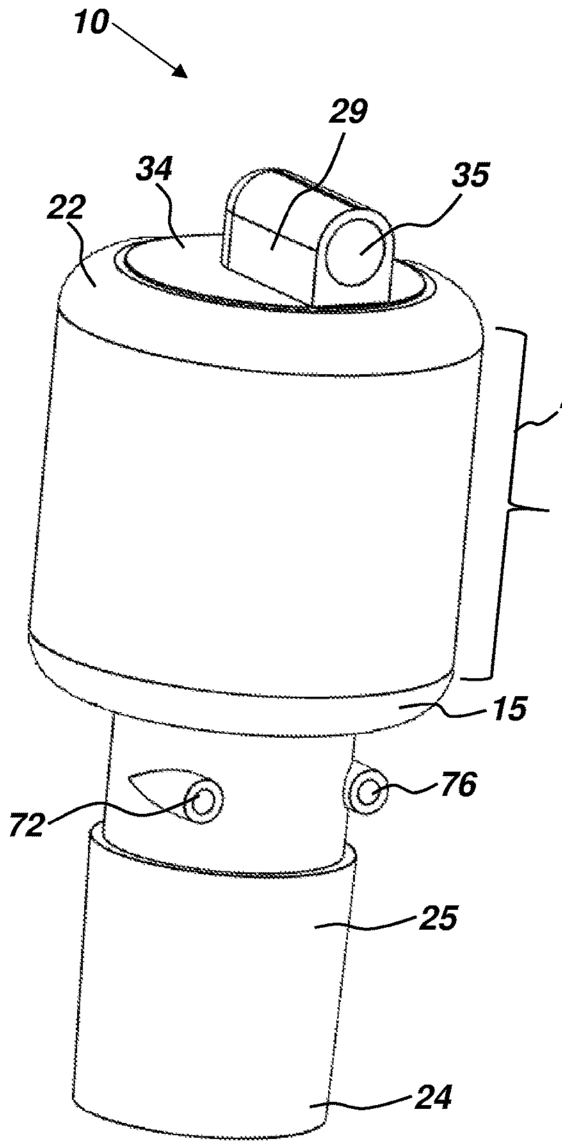
FIG. 3 is a perspective view of an exemplary adaptor.
Figure 4:
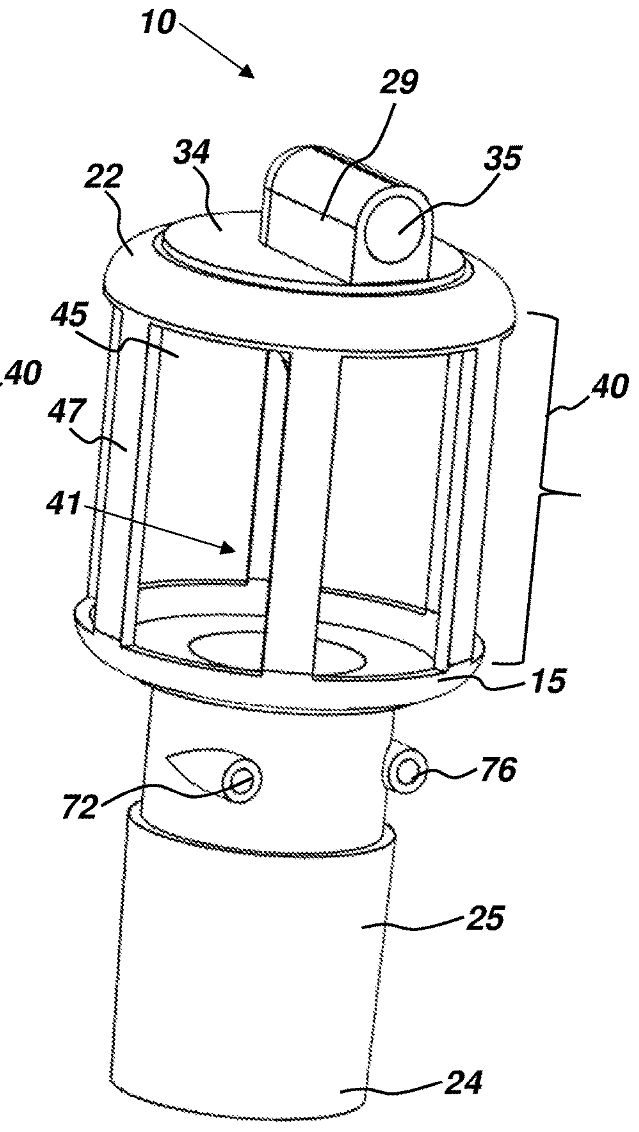
FIG. 4 is a perspective view of the adaptor of FIG. 3 with the flow-resisting media removed to show underlying structures.

FIGS. 2-4 illustrate one example of an adaptor 10. As best seen in FIG. 2, oxygen inlet 29 extends through the distal end 22 of the housing body 15, from the distal end exterior side 34 to the distal end interior side 36. Oxygen inlet 29 allows oxygen to be delivered into the distal air intake portion 40. A coupler 35 on the exterior side 34 of distal end 22 can couple oxygen inlet 29 to an oxygen source. Coupler can include an orifice which is sized to receive standard oxygen delivery tubing. Or the oxygen inlet 29 can be directly coupled to an oxygen source without a separate coupling structure provided.

Oxygen inlet 29 extends into the interior of the distal air intake portion 40 of the body 15 of the adaptor 10. As oxygen passes through the oxygen inlet 29 and into the distal air intake portion 40, the oxygen exits the oxygen inlet 29 through a nozzle 63 of the oxygen inlet 29, located on the proximal end of the oxygen inlet 29. Nozzle 63 includes one or more apertures 67 for directing the oxygen into the interior 41 of the distal air intake portion 40. One aperture, two apertures, or three or more apertures may be used to direct the oxygen from the oxygen inlet 29, through nozzle 63, and into the interior 41 of the distal air intake portion 40 of adaptor 10. For propelling nozzles 63 with two or more apertures 67, oxygen coming through the single-orificed coupler 35 on the distal end of the oxygen inlet 29 is split into multiple smaller orifices as it exits through nozzle 63.

The distal air intake portion 40 of the adaptor 10 operates on the Bernoulli principle of jet mixing of gas. Pure oxygen flows through one or more narrow apertures 67. This high-velocity stream entrains a constant proportion of room air through the air inlet port(s) 45 at the side of the distal air intake portion 40. This occurs because as the velocity of flow of oxygen increases, pressure at the side of the stream of flow decreases, thereby entraining more room air. Room air entrainment depends on the velocity of flow of the oxygen and the size of the air inlet port(s) 45.

In such configurations with a multiple-apertured nozzle 63, the use of multiple apertures 67 can allow equivalent air draw into the distal air intake portion 40 compared to a single aperture because of the surface area of the combined jets created by each of the apertures. To draw more air into the distal air intake portion 40, the area of the contact between the oxygen jet and the surrounding air can be increased. As a jet, plume or other stream of high velocity gas passes through stagnant gas, the high velocity gas rubs against or interfaces with the stagnant gas, and accelerates the stagnant gas, drawing it into the jet. By making the jet larger in diameter, or by giving it a more complex shape, it has a greater surface contact area with the stagnant gas so that more is drawn into the jet resulting in a greater total flow at the output. This Venturi device requires lower velocity to achieve the same amount of entrained air. By using multiple apertures 67 in a coordinated pattern for the apertures, a larger amount of air is drawn into the distal air intake portion while using a lower velocity. This lower velocity results in a quieter jet of oxygen.

One disadvantage of a high velocity accelerated jet of oxygen is unwanted acoustic noise. For traditional oxygen nozzles with a single aperture, the higher the velocity of the oxygen jet, the more turbulent the gas stream and the more noise the nozzle produces. When excessive, this noise may reduce the effectiveness of treatment. If the flow generator is too loud, it becomes a nuisance, interfering with patient sleep and the ability of clinicians to communicate while the flow generator is in use. By drawing or entraining ambient air using a lower velocity, the adaptor 10 can result in a quieter and better user experience.

The apertures 67 on the nozzle 63 are arranged to be placed generally in the center of the nozzle 63, with the nozzle 63 generally in the center relative to the outer dimensions of the adapter. FIGS. 7A through 15C show exemplary configurations of placement of the apertures 67 on nozzle 63. Other configurations and patterns for aperture placement are also possible.

Figure 17:
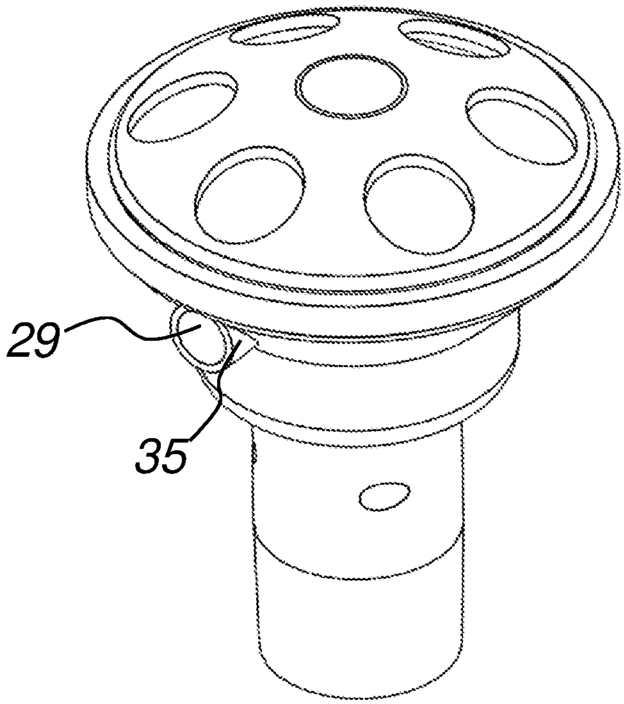
FIG. 17 is a perspective view of another exemplary nozzle.
Figure 18:
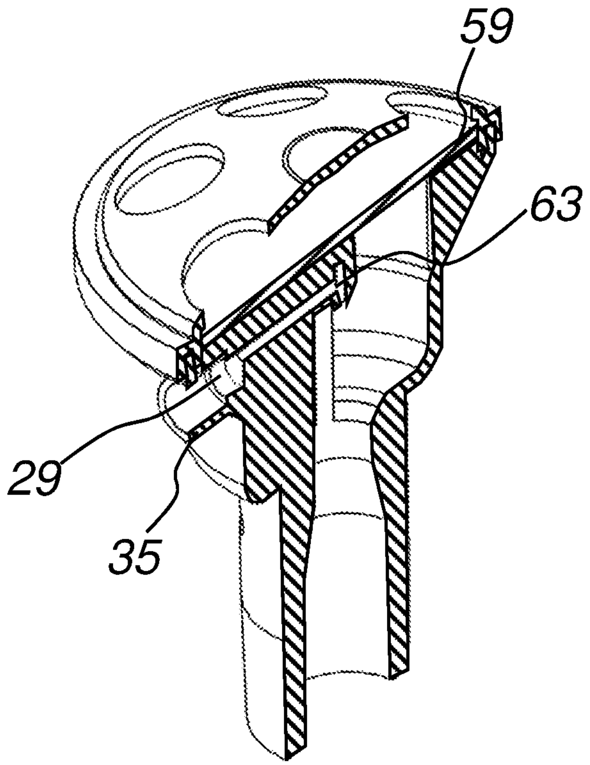
FIG. 18 a perspective, cross-sectional view of the exemplary nozzle of FIG. 17.
Figure 19:
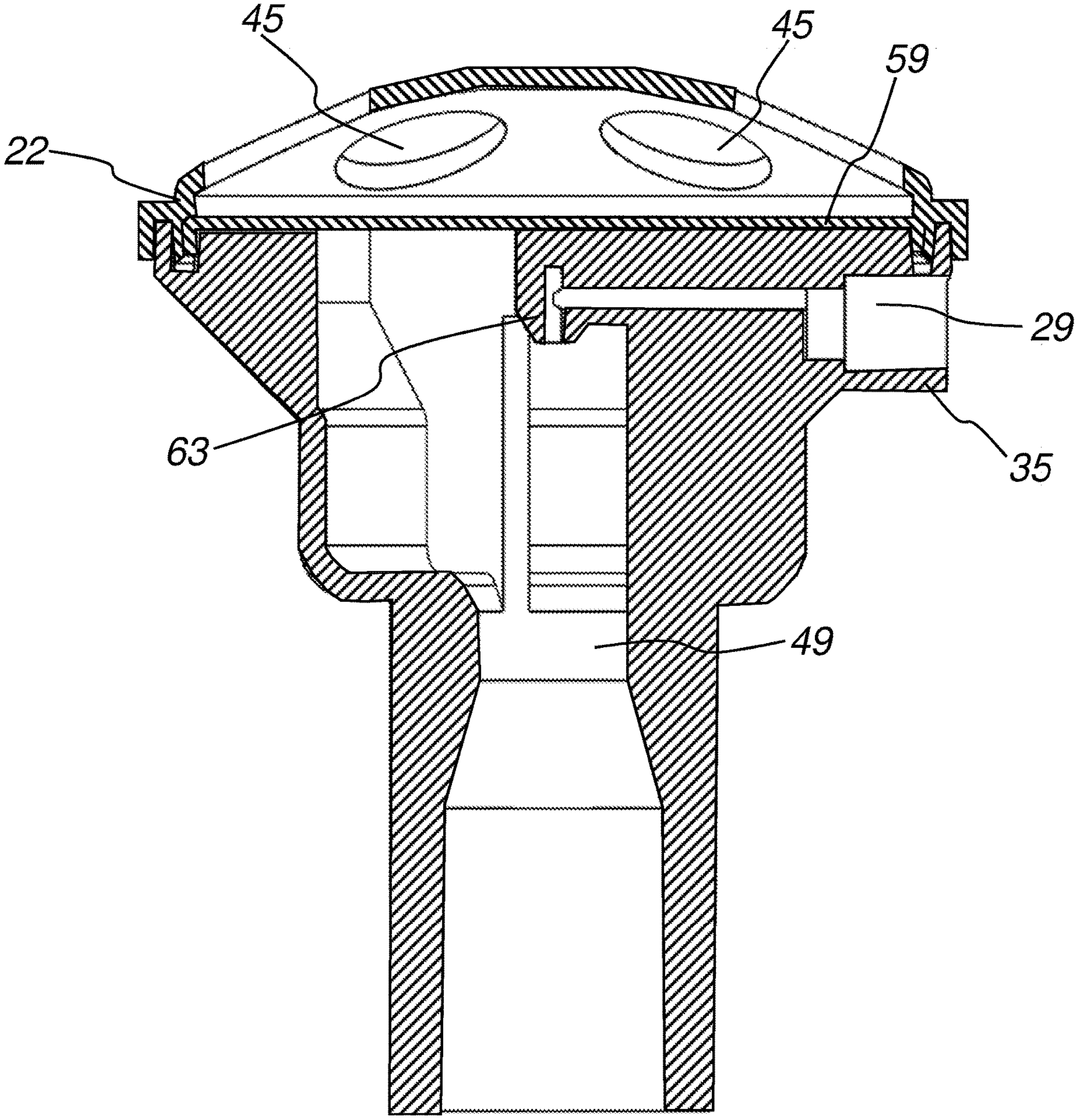
FIG. 19 is a side view of a cross-sectional view of the exemplary nozzle of FIG. 17.

FIGS. 17-19 show an exemplary configuration with the nozzle 63 in fluid communication with an oxygen air inlet 29 that comes in from the side of the device rather than the distal end 22. The distal end 22 includes a plurality of air inlet ports 45, and a flow-resisting media 59 between the air inlet ports 45 and the nozzle 63.

With the jet created by incoming oxygen through nozzle 63, additional air can be drawn into the distal air intake portion 40 as described above. One or more air inlet port(s) 45 allow air to be drawn into the distal air intake portion 40. One air inlet port 45 may be provided, or two or more air inlet ports 45 can be used. In the configuration shown in FIGS. 2-4, six air inlet ports 45 are shown, each generally the same size and shape. Fewer or more air inlet port(s) 45 can be used and the shape and size can vary among the air inlet ports 45. In the configuration shown in FIGS. 2-4, the distal air intake portion 40 is fairly open, with ribs 47 between each of the air inlet ports 45.

The area of air inlet port(s) 45 can vary based on the desired air mixing effects of the distal air intake portion 40. Air inlet port(s) 45 may be somewhat larger due to the flow-resisting media 59 that is placed over at least a portion of the air inlet port(s) 45 as described below. The area of the air inlet port(s) 45 may be larger than the area of the throat 49. In some examples, the total area of the air inlet port(s) 45 can be four times the area of the throat 49. In other examples, the total area of the air inlet port(s) 45 can be ten times the area of the throat or larger than ten times the area of the throat 49. Air inlet port(s) can be any desired shape and size.

In some examples, a flow-resisting media 59 is placed over one or more air inlet ports 45. FIGS. 3 and 4 show the adaptor 10 with the flow-resisting media 59 in place (FIG. 3) and without the flow-resisting media 59 in place (FIG. 4). The flow-resisting media 59 covering the air inlet port(s) 45 restricts the amount of air drawn into the distal air intake portion 40 when flow at the outlet 26 or exit port is limited. In some examples, the flow-resisting media 59 covers only a portion of the air inlet port(s) and in other examples the flow-resisting media 59 covers the entire air inlet port(s) 45.

Figure 16:
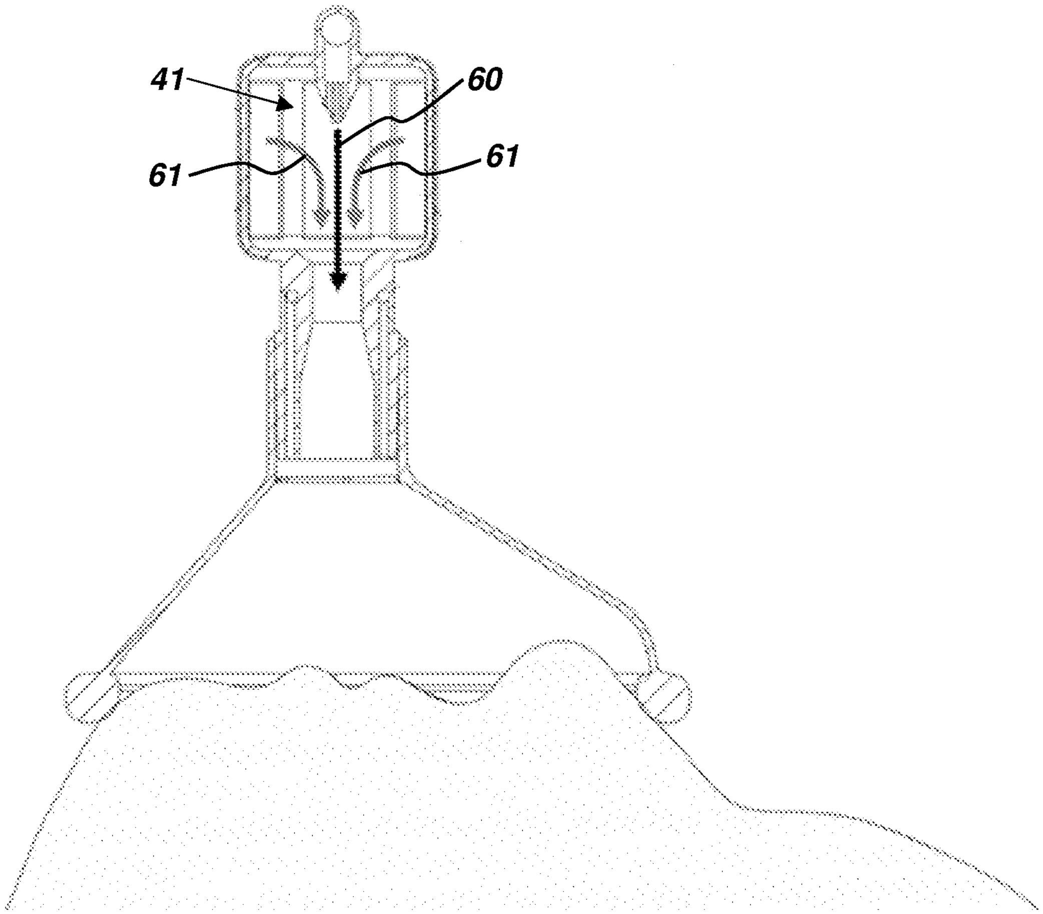
FIG. 16 is a side, elevation, cross-sectional view of an exemplary adaptor in place on a mask of a patient.

As seen in FIG. 16, flow within the adaptor 10 includes the incoming flow from oxygen (indicated at arrow 60), as well as incoming entrained ambient air pulled in through air intake(s) 45 by the oxygen jet created by nozzle 63 (indicated by arrows 61). Flow-resisting media 59 resists the incoming flow pulled in by the oxygen jet through air inlet port(s) 45. That is, flow that is indicated by arrows 61 has to overcome the flow-resisting media 59 before it can enter the interior 41 of the distal air intake portion 40.

Flow at the outlet 26 is typically limited during the patient's end expiratory pause of the patient's breath (or other phases of the breath during which flow through the outlet 26 or exit port is restricted). In most spontaneously breathing patients, a breath can be divided into three phases. The first phase is inspiration, during which the lungs expand, creating a negative pressure at the outlet 26 which actively draws air into the lungs. Inspiration is followed by the expiratory phase, during which gas is forced or passively allowed to leave the lungs. The third phase of respiration that is often, but not always, observed is an end expiratory pause where gas is neither moving into or out of the lungs while waiting for the next inspiration to begin. During this end expiratory pause, flow at the outlet 26 is limited.

When flow at the outlet 26 is limited, flow-resisting media 59 limits ambient air from being drawn into the distal air intake portion 40 through the air inlet port(s) 45. Because flow is reduced at the outlet 26, ambient air has a harder time overcoming the flow-resisting media 59 to enter the distal air intake portion 40. When less ambient air is drawn into the distal air intake portion 40, the gas at the outlet 26 of adaptor 10 is comprised mostly of oxygen coming in through the nozzle 63 of the oxygen inlet 29. Ambient airflow indicated by arrows 61 in FIG. 16 is limited when flow is reduced at the outlet 26, but oxygen flow indicated by arrow 60 is not limited. Therefore gas at the outlet 26 can approach pure oxygen at the end expiratory pause.

Higher oxygen concentration during the pause phase of the patient's breathing (or the end of the expiratory phase where there is no pause) causes the mask or other user interface to be filled with gas having a high oxygen concentration. Because most masks allow a small amount of mask leak, the mask volume is at least partially flushed with gas from the adaptor 10 during the expiratory pause. Even when there is no mask leak, gas flowing from the nozzle 63 out through the outlet 26 flushes the mask 28 with near 100% oxygen. This means that when the patient inhales, the first gas that enters the lungs will be the high oxygen concentration gas in the mask 28. The amount of oxygen the patient inhales is increased if the adaptor 10 outputs higher concentration of oxygen when its output flow is restricted. In most situations where patient respiration requires support and a CPAP adapter is needed, it is preferred that the patient inhale a higher concentration of oxygen while still receiving adequate flow and pressure from the adapter. By using flow-resisting media to limit ambient air entrainment (but not limit oxygen flow), this higher concentration of oxygen can be achieved.

Flow-resisting media 59 can include filtration media such as Technostat® 90 Plus manufactured by Superior Felt & Filtration, which is a combination of spun-bond polypropylene filter media and supporting scrim. Other Technostat® scrim or non-Technostat® scrim could be used. A layer of scrim alone or filter media alone could also be used to resist flow and create the oxygen concentration elevating effect as well. Or a mesh screen material or any material or area with a plurality of small holes, or an arrangement of small holes, could be used to resist flow and act as flow-resisting media 59. Cloth or any other resistive material could also be used. Resistive material or flow-resisting media 59 can have other functionalities, as desired. For example, antibacterial materials could be used to for the flow-resisting media 59 such that the flow-resisting media 59 has antibacterial properties.

In some examples, the flow restriction over the air inlet port(s) 45 provides a linear resistance to flow response. That is, if the flow is doubled, the created pressure drop across the flow-resisting media 59 would be doubled as well. Filter media made up of a mesh of many small area orifices such as fine screen or a cloth filter, or scrim media, can provide a linear resistance. In contrast, larger orifices tend to have a nonlinear flow. However, flow-resisting media 59 with larger orifices can also be used in some examples.

Oxygen flowing into the distal air intake portion 40 mixes with air pulled into the distal air intake portion 40 through the air inlet port(s) 45 (which air inlet port(s) 45 can be fully or partially covered with flow-resisting media 59). This mixed air is pulled proximally through a throat 49 and through the outlet 26 as the patient inhales and pulls the mixed air into the user interface (such as mask 28) to breathe in. Throat 49 has a first circumference, and outlet 26 has a second circumference. In one example, the first throat circumference is less than the second outlet circumference. Similarly, the throat circumference can be less than the circumference of the distal air intake portion 40. In other examples, the throat circumference is equal to or greater than the outlet circumference and/or the circumference of the distal air intake portion 40. The size of the throat should be large enough to not constrict airflow as the patient breathes out.

Figure 5:
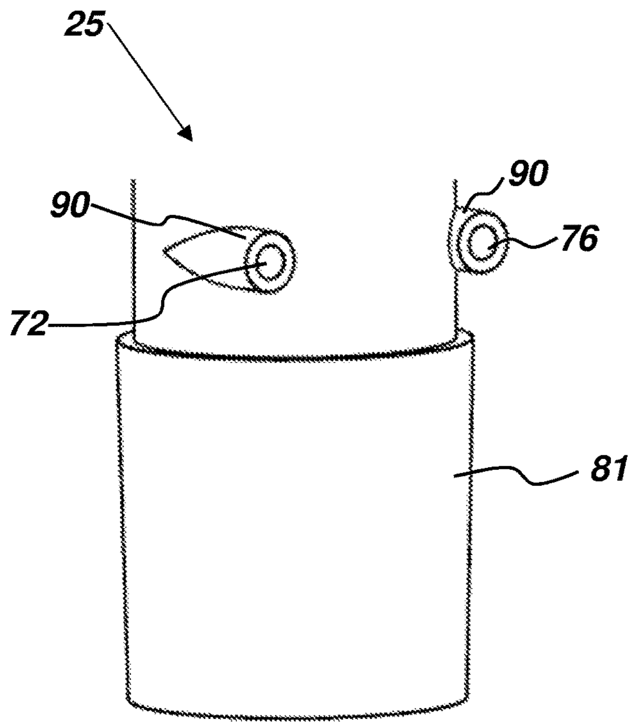
FIG. 5 is a perspective view of a proximal portion of an adaptor.
Figure 6:
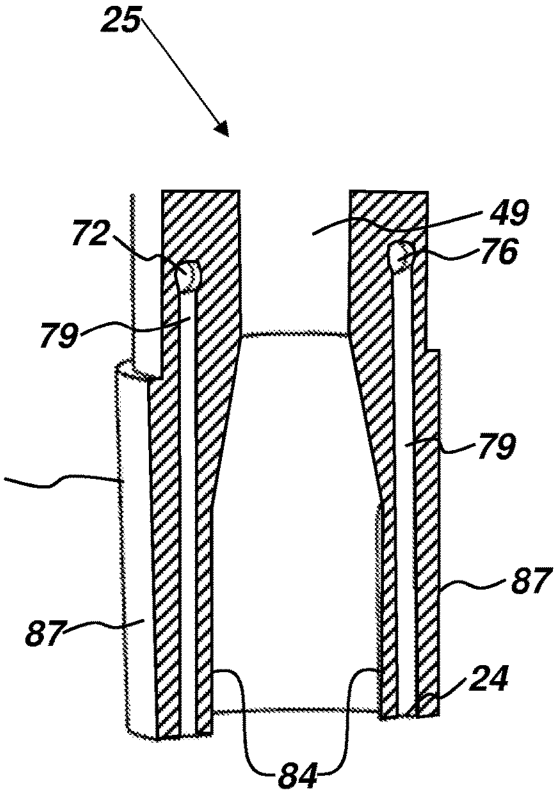
FIG. 6 is a perspective, cross-sectional view of the proximal portion of the adaptor of FIG. 5.
Figure 7A:
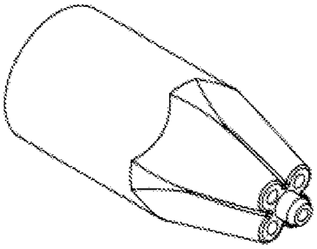
FIG. 7A is a perspective view of an exemplary nozzle.
Figure 8A:
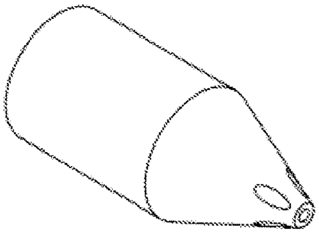
FIG. 8A is a perspective view of an exemplary nozzle.
Figure 9A:
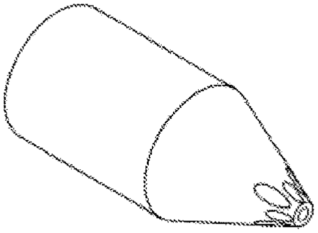
FIG. 9A is a perspective view of an exemplary nozzle.
Figure 7B:
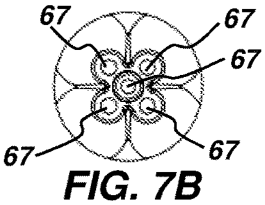
FIG. 7B is a proximal end view of the exemplary nozzle of FIG. 7A.
Figure 8B:
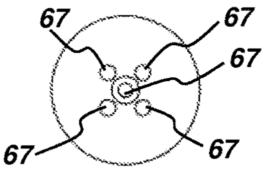
FIG. 8B is a proximal end view of the exemplary nozzle of FIG. 8A.
Figure 9B:
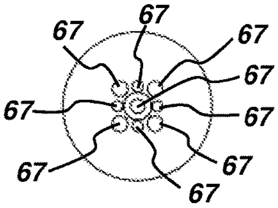
FIG. 9B is a proximal end view of the exemplary nozzle of FIG. 9A.
Figure 7C:
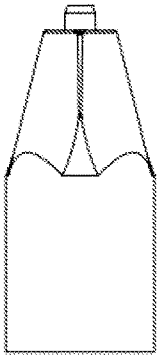
FIG. 7C is a side view of the exemplary nozzle of FIGS. 7A and 7B.
Figure 8C:
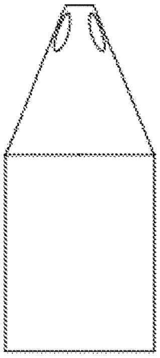
FIG. 8C is a side view of the exemplary nozzle of FIGS. 8A and 8B.
Figure 9C:
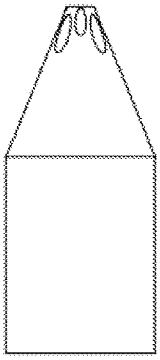
FIG. 9C is a side view of the exemplary nozzle of FIGS. 9A and 9B.
Figure 10A:
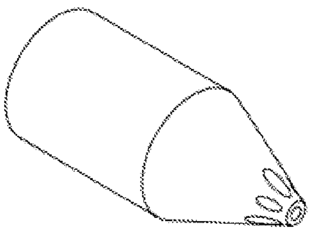
FIG. 10A is a perspective view of an exemplary nozzle.
Figure 11A:
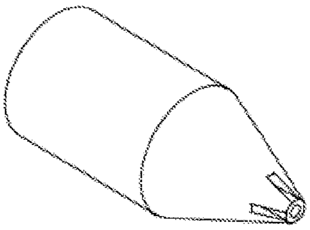
FIG. 11A is a perspective view of an exemplary nozzle.
Figure 12A:
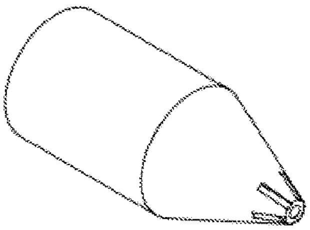
FIG. 12A is a perspective view of an exemplary nozzle.
Figure 10B:
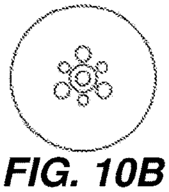
FIG. 10B is a proximal end view of the exemplary nozzle of FIG. 10A.
Figure 11B:
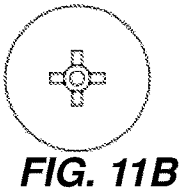
FIG. 11B is a proximal end view of the exemplary nozzle of FIG. 11A.
Figure 12B:
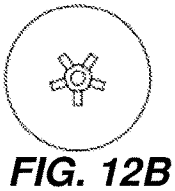
FIG. 12B is a proximal end view of the exemplary nozzle of FIG. 12A.
Figure 10C:
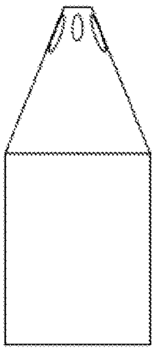
FIG. 10C is a side view of the exemplary nozzle of FIGS. 10A and 10B.
Figure 11C:
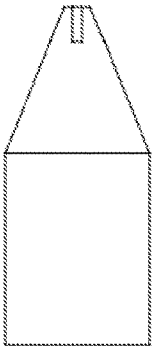
FIG. 11C is a side view of the exemplary nozzle of FIGS. 11A and 11B.
Figure 12C:
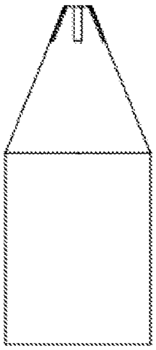
FIG. 12C is a side view of the exemplary nozzle of FIGS. 12A and 12B.
Figure 13A:
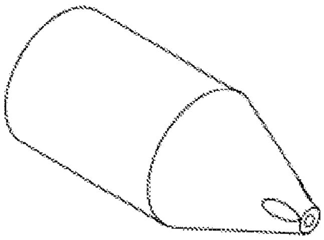
FIG. 13A is a perspective view of an exemplary nozzle.
Figure 14A:
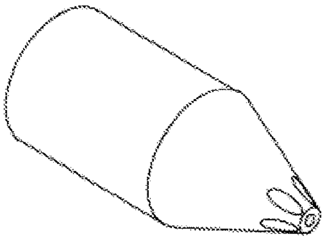
FIG. 14A is a perspective view of an exemplary nozzle.
Figure 15A:
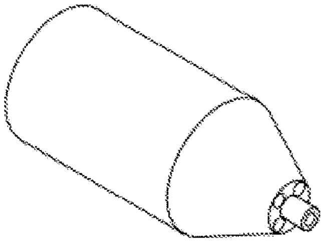
FIG. 15A is a perspective view of an exemplary nozzle.
Figure 13B:
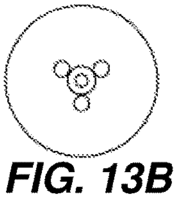
FIG. 13B is a proximal end view of the exemplary nozzle of FIG. 13A.
Figure 14B:
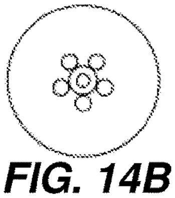
FIG. 14B is a proximal end view of the exemplary nozzle of FIG. 14A.
Figure 15B:
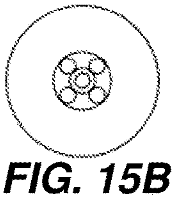
FIG. 15B is a proximal end view of the exemplary nozzle of FIG. 15A.
Figure 13C:
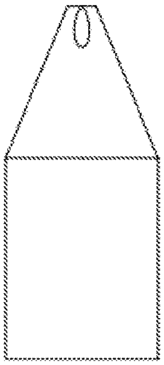
FIG. 13C is a side view of the exemplary nozzle of FIGS. 13A and 13B.
Figure 14C:
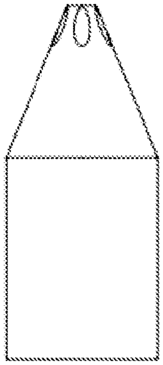
FIG. 14C is a side view of the exemplary nozzle of FIGS. 14A and 14B.
Figure 15C:
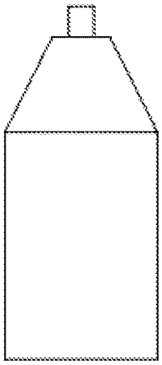
FIG. 15C is a side view of the exemplary nozzle of FIGS. 15A and 15B.

In some examples, the adaptor 10 also includes one or more ports for enabling measurement. FIGS. 5-6 illustrates the proximal portion 25 of the adaptor 10 with a pressure measuring port 72 and a gas sampling port 76. In other configurations, only a pressure measuring port 72 or only a gas sampling port 76 are provided. One or more ports can be formed by providing a lumen 79 formed within the interior of the sidewall 81 of the proximal portion 25, between an interior 84 and an exterior 87 of the sidewall 81. The lumen 79 can extend from a coupler 90 to the proximal end 24 of the adaptor 10. The lumen 79 can be open on the proximal end 24 to allow the lumen 79 to be in fluid communication with the air in the mask of the patient. The coupler 90 can extend from the lumen 79 through the sidewall 81 to the exterior 87 of the sidewall 81. Coupler 90 can be used to couple the lumen 79 to a measuring device (such as a pressure-measuring device and/or a gas sampling device).

It can be helpful during CPAP therapy to monitor the pressure in the mask as well as the concentration of oxygen and/or carbon dioxide in the mask. To facilitate this monitoring, the adaptor 10 can incorporates ports that include lumen(s) 79 in the sidewall 81 of the proximal portion 25. Lumen(s) 79 can be narrow to increase accuracy of measurements, particularly for gas sampling. These lumens 79 open on, or near, the proximal end 24 of the adaptor 10—which is coupled to the patient's mask—so that the pressure in the mask and/or concentration of gas in the mask can be measured using a tube connected to one of these lumens via coupler 90. Placement of the port openings on the face of the proximal end 24, rather than within the adapter 10, can be more accurate because measurement at that point is more representative of mask pressure and respired gas concentration compared to measurement within the adaptor 10. For gas sampling in particular, much more accurate readings are obtained when the reading is taken closer to the patient.

In use, the adapter is connected to a patient interface, such as a tight-fitting breathing mask. The mask can be held on the patient's face either manually or using a fastening strap placed around the patient's head and secured to the mask. The coupler 35 on distal end 22 can be attached to an oxygen source. Once the coupler 35 is attached to an oxygen source, oxygen can be provided to adaptor 10 from an oxygen source through oxygen inlet 29. Optionally, pressure measurement and gas concentration measurement devices can also be connected to the adaptor, at pressure measuring port 72 and a gas sampling port 76, respectively.

As oxygen passes through oxygen inlet 29, a high velocity accelerated jet of gas is created by passing the high-pressure oxygen through the propelling nozzle 63 of oxygen inlet 29 that includes one or more apertures 67. In some examples, multiple apertures 67 are used to create the necessary air entrainment at a lower velocity to reduce the noise created by adaptor 10. The jet of oxygen exiting the nozzle 63 entrains surrounding ambient air into the distal air intake portion 40 of adapter 10 and accelerates the ambient air such that when flow is unobstructed, the total flow at the outlet 26 of the adapter 10 is much greater than the flow of oxygen passing through the propelling nozzle 63.

As the patient comes to the end of a breath, flow at the outlet 26 is obstructed, and flow-resisting media 59 limits the amount of ambient air entrained within distal air intake portion 40. The concentration of oxygen increases until the adaptor 10 (and/or mask 28) is flush with pure oxygen. As the patient begins to inhale at the end of the expiratory pause, the patient inhales air with a high concentration of oxygen.

Additionally, adaptor 10 can be connected at one coupler 90 to a gas sampling device and can be connected at the other coupler 90 to a pressure measuring device. During CPAP therapy, the gas sampling device can take gas sampling measurements at the proximal end 24 of adaptor 10 which is in fluid communication with the mask 28. Similarly, the pressure measuring device can take pressure measurements at the proximal end 24 of adaptor 10 which is in fluid communication with the mask 28. By taking these measurements at the mask (rather than within the body of the adapter 10), a more accurate measurement can be obtained.

The description is only exemplary of the principles of the disclosure, and should not be viewed as narrowing the scope of the claims which follow, which claims define the full scope of the invention. Various aspects discussed in one drawing may be present and/or used in conjunction with the embodiment shown in another drawing, and each element shown in multiple drawings may be discussed only once. The described features, structures, or characteristics of configurations of the disclosure may be combined in any suitable manner in one or more configurations. In some cases, detailed description of well-known items or repeated description of substantially the same configurations may be omitted to facilitate the understanding of those skilled in the art by avoiding an unnecessarily redundant description. All statements herein reciting principles, aspects, and embodiments of the invention, as well as specific examples thereof, are intended to encompass equivalents thereof.

Reference in the specification to "one configuration" "one embodiment," "a configuration" "an example," or "an embodiment" means that a particular feature, structure, or characteristic described in connection with the configuration is included in at least one configuration, but is not a requirement that such feature, structure or characteristic be present in any particular configuration unless expressly set forth in the claims as being present. The appearances of the phrase "in one configuration" or "in one example" in various places may not necessarily limit the inclusion of a particular element of the disclosure to a single configuration, rather the element may be included in other or all configurations discussed herein.

As used in this specification and the appended claims, singular forms such as "a," "an," and "the" may include the plural unless the context clearly dictates otherwise. Thus, for example, reference to "a jet" may include one or more of such jets, and reference to "the injection port" may include reference to one or more of such ports.

As used herein, the term "generally" refers to something that is more of the designated adjective than not, or the converse if used in the negative. As used herein, the term "about" is used to provide flexibility to a numerical range endpoint by providing that a given value may be "a little above" or "a little below" the endpoint while still accomplishing the function associated with the range, for example, "about" may be within 10% of the given number or given range. As used herein, a plurality of items, structural elements, compositional elements, and/or materials may be presented in a common list for convenience. However, these lists should be construed as though each member of the list is individually identified as a separate and unique member.

Numerical data may be expressed in a range format. This range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. For example, a numerical range of "about 5 to about 60" should be interpreted to include not only the explicitly recited values of about 1 to about 5, but also include individual values and sub-ranges within the indicated range. Thus, included in this numerical range are individual values such as 6, 7, 8, 9, etc., through 60, and sub-ranges such as from 10-20, from 30-40, and from 50-60, etc., as well as each number individually. This same principle applies to ranges reciting only one numerical value as a minimum or a maximum. Furthermore, such an interpretation should apply regardless of the breadth of the range or the characteristics being described.

While methods are described herein in discrete steps in a particular order for the sake of clarity, the steps do not require a particular order and more than one step may be performed at the same time. For example, a later step may begin before earlier step completes. Or, a later step may be completed before an earlier step is started. Additionally, the word "connected" and "coupled" is used throughout for clarity of the description and can include either a direct connection or an indirect connection.

Aspect 1: An adaptor for generating flow, the adaptor comprising:

an adaptor housing body, the adaptor housing body comprising a distal end and an open proximal end for attachment to a patient interface;

the distal end of the adaptor housing body having an oxygen inlet, the oxygen inlet comprising a coupler on an exterior side for connection to an oxygen source, the oxygen inlet extending into an interior of a distal air intake portion, and the oxygen inlet having a nozzle with at least two apertures for directing oxygen into an interior of a distal air intake portion;

the distal air intake portion comprising at least one air inlet port to allow air to be drawn into the interior of the distal air intake portion, a proximal portion in communication with the distal air intake portion, the proximal portion forming a throat having a first circumference and an outlet having a second circumference for connection to a patient interface, the first circumference being smaller than the second circumference, the proximal portion further comprising at least one of a pressure measuring port and a gas sampling port.

Aspect 2: The adaptor of Aspect 1, further comprising a flow-resisting media covering at least a portion of the at least one air inlet port.

Aspect 3: The adaptor of Aspect 1 or Aspect 2, wherein the air inlet port has a first area and the throat has a second area, and where in the first area is at least four times larger than the second area.

Aspect 4: The adaptor of any of Aspects 1-3, wherein the flow-resisting media entirely covers the at least one air inlet port.

Aspect 5: The adaptor of any of Aspects 1-4, wherein at least one of the pressure measuring port and the gas sampling port comprise a lumen formed in the interior of a sidewall of the proximal portion, between an interior and an exterior of the sidewall of the proximal portion; and the lumen extending from a coupler open to the exterior of the proximal portion for attachment to a measurement device, to the proximal open end of the adaptor, the lumen being open on the open proximal end of the adaptor to allow the lumen to be in fluid communication with the air in a mask of a patient.

Aspect 6: The adaptor of any of Aspects 1-5, wherein the oxygen inlet comprises at least three apertures for directing oxygen into an interior of a distal air intake portion.

Aspect 7: The adaptor of any of Aspects 1-6, wherein the at least three apertures are spaced equidistant apart and the at least three apertures are the same shape and size.

Aspect 8: The adaptor of any of Aspects 1-7, wherein the at least one air inlet port comprises at least two air inlet ports, and wherein the at least two air inlet ports have a total area that is at least four times a total area of the throat.

Aspect 9: An adaptor for generating flow, the adaptor comprising:

an adaptor housing body, the adaptor housing body extending from a distal end to an open proximal end, the open proximal end for attachment to a patient mask;

the distal end of the adaptor housing body having an oxygen inlet for coupling to an oxygen source, the oxygen inlet extending into an interior of a distal air intake portion, and the oxygen inlet having a nozzle with at least one aperture for directing oxygen into the interior of a distal air intake portion; and the distal air intake portion comprising at least one air inlet port to allow ambient air to be drawn into the interior of the distal air intake portion, a flow-resisting media covering at least a portion of the at least one air inlet port.

Aspect 10: The adaptor of Aspect 9, wherein the at least one aperture comprises two or more apertures.

Aspect 11: The adaptor of Aspect 9 or Aspect 10, further comprising a proximal portion in communication with the distal air intake portion, the proximal portion forming a throat.

Aspect 12: The adaptor of any of Aspects 9-11, wherein the proximal portion further comprises at least one of a pressure measuring port and a gas sampling port.

Aspect 13: The adaptor of any of Aspects 9-12, wherein at least one of the pressure measuring port and the gas sampling port comprise a lumen formed in the interior of a sidewall of the proximal portion, between an interior and an exterior of the sidewall of the proximal portion; and the lumen extending from a coupler open to the exterior of the proximal portion for attachment to a measurement device, to the proximal open end of the adaptor, the lumen being open on the open proximal end of the adaptor to allow the lumen to be in fluid communication with air in a mask of a patient.

Aspect 14: The adaptor of any of Aspects 9-13, wherein the throat has a first circumference and an outlet has a second circumference for connection to a patient interface, the first circumference being smaller than the second circumference.

Aspect 15: The adaptor of any of Aspects 9-14, wherein the nozzle comprises at least three apertures for directing oxygen into the interior of a distal air intake portion, the at least three apertures spaced equidistant apart and the at least three apertures having the same shape and size.

Aspect 16: The adaptor of any of Aspects 9-15, wherein the at least one air inlet port comprises at least two air inlet ports, and wherein the at least two air inlet ports have a total area that is at least ten times a total area of the throat.

Aspect 17: An adaptor for generating flow, the adaptor comprising:

an adaptor housing body, the adaptor housing body comprising a distal end and an open proximal end for attachment to a patient interface;

the distal end of the adaptor housing body having an oxygen inlet, the oxygen inlet comprising a coupler on an exterior side for connection to an oxygen source to convey pressurized oxygen from a pressurized oxygen source in connection with the coupler to the adaptor;

the oxygen inlet extending into an interior of a distal air intake portion, and the oxygen inlet having a nozzle with at least two apertures for directing oxygen into an interior of a distal air intake portion; and the distal air intake portion comprising at least one air inlet port to allow air to be drawn into the interior of the distal air intake portion, and a flow-resisting media covering at least a portion of the at least one air inlet port.

Aspect 18: The adaptor of Aspect 17, further comprising a proximal portion in communication with the distal air intake portion, the proximal portion forming a throat having a first circumference and an outlet having a second circumference for connection to a patient interface, the first circumference being smaller than the second circumference, the proximal portion further comprising a pressure measuring port and a gas sampling port.

Aspect 19: The adaptor of Aspect 17 or 18, wherein at least one of the pressure measuring port and the gas sampling port comprise a lumen formed in the interior of a sidewall of the proximal portion, between an interior and an exterior of the sidewall of the proximal portion, the lumen extending from a coupler open to the exterior of the proximal portion for attachment to a measurement device, to the open proximal end of the adaptor, the lumen being open on the open proximal end of the adaptor.

Aspect 20: The adaptor of any of Aspects 17-19, wherein the nozzle comprises at least three apertures for directing oxygen into the interior of a distal air intake portion, the at least three apertures spaced equidistant apart and the at least three apertures having the same shape and size.

Although the foregoing disclosure provides many specifics, it will be appreciated that other applications contemplated and these should not be construed as limiting the scope of any of the ensuing claims. Other embodiments and configurations may be devised which do not depart from the scopes of the claims. Features from different embodiments and configurations may be employed separately or in combination. Accordingly, all additions, deletions and modifications to the disclosed subject matter that fall within the scopes of the claims are to be embraced thereby. The scope of each claim is indicated and limited only by its plain language and the full scope of available legal equivalents to its elements.

Furthermore, if any references have been made to patents and printed publications throughout this disclosure, each of these references and printed publications are individually incorporated herein by reference in their entirety.

The invention claimed is:

1. An adaptor for generating flow, the adaptor comprising:

an adaptor housing body, the adaptor housing body comprising a distal end and an open proximal end for attachment to a patient interface;

the distal end of the adaptor housing body having an oxygen inlet, the oxygen inlet comprising a coupler on an exterior side for connection to an oxygen source, the oxygen inlet extending into an interior of a distal air intake portion, and the oxygen inlet having a nozzle with at least two apertures for directing oxygen into the interior of the distal air intake portion;

the distal air intake portion comprising at least one air inlet port to allow air to be drawn into the interior of the distal air intake portion, a proximal portion in communication with the distal air intake portion, the proximal portion forming a throat having a first circumference and an outlet having a second circumference for connection to a patient interface, the first circumference being smaller than the second circumference, the proximal portion further comprising at least one of a pressure measuring port and a gas sampling port downstream of the throat.

2. The adaptor of claim 1, further comprising a flow-resisting media covering at least a portion of the at least one air inlet port.

3. The adaptor of claim 2, wherein the at least one air inlet port has a first total area and the throat has a second area, and wherein the first total area is at least four times larger than the second area.

4. The adaptor of claim 2, wherein the flow-resisting media entirely covers the at least one air inlet port.

5. The adaptor of claim 1, wherein at least one of the pressure measuring port and the gas sampling port comprise a lumen formed within a sidewall of the proximal portion, between an interior and an exterior of the sidewall of the proximal portion; and the lumen extending from a coupler open to the exterior of the sidewall of the proximal portion for attachment to a measurement device, to the proximal open end of the adaptor, the lumen being open on the open proximal end of the adaptor to allow the lumen to be in fluid communication with the air in the patient interface of a patient.

6. The adaptor of claim 1, wherein the nozzle of the oxygen inlet comprises at least three apertures for directing oxygen into the interior of the distal air intake portion.

7. The adaptor of claim 6, wherein the at least three apertures are spaced equidistant apart and the at least three apertures are the same shape and size.

8. The adaptor of claim 1, wherein the at least one air inlet port comprises at least two air inlet ports, and wherein the at least two air inlet ports have a total area that is at least four times a total area of the throat.

9. An adaptor for generating flow, the adaptor comprising:
an adaptor housing body, the adaptor housing body extending from a distal end to an open proximal end, the open proximal end for attachment to a patient mask;
the distal end of the adaptor housing body having an oxygen inlet for coupling to an oxygen source, the oxygen inlet extending into an interior of a distal air intake portion, and the oxygen inlet having a nozzle with at least one aperture for directing oxygen into the interior of the distal air intake portion; and
a proximal portion in communication with the distal air intake portion, the proximal portion forming a throat, the distal air intake portion comprising at least one air inlet port to allow ambient air to be drawn into the interior of the distal air intake portion, the at least one air inlet port between the nozzle and the throat of the proximal portion.

10. The adaptor of claim 9, wherein the at least one aperture comprises two or more apertures.

11. The adaptor of claim 9, further comprising a proximal portion in communication with the distal air intake portion, the proximal portion forming a throat.

12. The adaptor of claim 11, wherein the proximal portion further comprises at least one of a pressure measuring port and a gas sampling port.

13. The adaptor of claim 12, wherein at least one of the pressure measuring port and the gas sampling port comprise a lumen formed within a sidewall of the proximal portion, between an interior and an exterior of the sidewall of the proximal portion; and
the lumen extending from a coupler open to the exterior of the sidewall of the proximal portion for attachment to a measurement device, to the proximal open end of the adaptor, the lumen being open on the open proximal end of the adaptor to allow the lumen to be in fluid communication with air in the patient mask.

14. The adaptor of claim 11, wherein the throat has a first circumference and an outlet has a second circumference for connection to the patient mask, the first circumference being smaller than the second circumference.

15. The adaptor of claim 9, wherein the nozzle comprises at least three apertures for directing oxygen into the interior of the distal air intake portion, the at least three apertures spaced equidistant apart and the at least three apertures having the same shape and size.

16. The adaptor of claim 11, wherein the at least one air inlet port comprises at least two air inlet ports, and wherein the at least two air inlet ports have a total area that is at least ten times a total area of the throat.

17. An adaptor for generating flow, the adaptor comprising:
an adaptor housing body, the adaptor housing body comprising a distal end and an open proximal end for attachment to a patient interface;
the distal end of the adaptor housing body having an oxygen inlet, the oxygen inlet for coupling to an oxygen source to convey pressurized oxygen from a pressurized oxygen source to the adaptor;
the oxygen inlet extending into an interior of a distal air intake portion, and the oxygen inlet having a nozzle for directing oxygen into the interior of the distal air intake portion;
the distal air intake portion comprising at least one air inlet port to allow air to be drawn into the interior of the distal air intake portion; and
a proximal portion in communication with the distal air intake portion, the proximal portion forming a throat and the proximal portion comprising a pressure measuring port and/or a gas sampling port downstream of the throat.

18. The adaptor of claim 17, wherein the proximal portion forming the throat has a first circumference and an outlet having a second circumference for connection to the patient interface, the first circumference being smaller than the second circumference.

19. The adaptor of claim 18, wherein at least one of the pressure measuring port and the gas sampling port comprise a lumen formed within a sidewall of the proximal portion, between an interior and an exterior of the sidewall of the proximal portion, the lumen extending from a coupler open to the exterior of the sidewall of the proximal portion for attachment to a measurement device, to the open proximal end of the adaptor, the lumen being open on the open proximal end of the adaptor.

20. The adaptor of claim 17, wherein the nozzle comprises at least three apertures for directing oxygen into the interior of the distal air intake portion, the at least three apertures spaced equidistant apart and the at least three apertures having the same shape and size.

* * * * *